(12) United States Patent
Moriuchi et al.

(10) Patent No.: US 6,200,337 B1
(45) Date of Patent: *Mar. 13, 2001

(54) IMPLANTING STENT

(75) Inventors: Yousuke Moriuchi; Toshinari Asaka, both of Shizuoka-ken; Masakiyo Nobuyoshi, Fukuoka-ken, all of (JP)

(73) Assignee: Terumo Kabushiki Kaisha, Shibuya-Ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/195,437

(22) Filed: Nov. 18, 1998

Related U.S. Application Data

(62) Division of application No. 08/814,040, filed on Mar. 10, 1997, now Pat. No. 5,879,381.

(30) Foreign Application Priority Data

Mar. 10, 1996 (JP) .................................................. 8-082072

(51) Int. Cl.⁷ ...................................................... A61F 2/06
(52) U.S. Cl. ........................ 623/1.16; 623/23.7; 623/1.17; 606/198
(58) Field of Search .............................. 623/1, 12, 1.16, 623/23.7, 1.15, 1.17; 606/191, 195, 198

(56) References Cited

U.S. PATENT DOCUMENTS

| | | |
|---|---|---|
| 4,733,665 | 3/1988 | Palmaz . |
| 4,762,128 | 8/1988 | Rosenbluth . |
| 4,776,337 | 10/1988 | Palmaz . |
| 5,019,090 | 5/1991 | Pinchuk . |
| 5,092,877 | 3/1992 | Pinchuk . |
| 5,102,417 | 4/1992 | Palmaz . |
| 5,133,732 | 7/1992 | Wiktor . |
| 5,195,984 | 3/1993 | Schatz . |
| 5,226,913 | 7/1993 | Pinchuk . |
| 5,370,683 | 12/1994 | Fontaine . |
| 5,421,955 | 6/1995 | Lau et al. . |
| 5,443,498 | 8/1995 | Fontaine . |
| 5,449,373 | 9/1995 | Pinchasik et al. . |
| 5,591,197 | 1/1997 | Orth et al. . |
| 5,707,386 | 1/1998 | Schnepp-Pesch et al. . |
| 5,728,158 | 3/1998 | Lau et al. . |
| 5,879,381 * | 3/1999 | Moriuchi et al. .................... 623/1.16 |
| 5,906,639 * | 5/1999 | Rudnick et al. ........................ 623/1 |
| 6,053,940 * | 4/2000 | Wijay ...................................... 623/1 |

FOREIGN PATENT DOCUMENTS

| | | |
|---|---|---|
| 0 540 290 | 5/1993 | (EP) . |
| 0 688 545 | 12/1995 | (EP) . |

* cited by examiner

*Primary Examiner*—Paul B. Prebilic
(74) *Attorney, Agent, or Firm*—Burns, Doane, Swecker & Mathis, LLP

(57) ABSTRACT

A stent in the form of a generally tubular member has a diameter allowing for insertion into a body passageway and is radially expandable upon application of an outward force. A series of annular units are axially arranged to construct the stent. Each annular unit includes a plurality of generally ellipsoidal or polygonal elements equiangularly arranged around the stent axis, the elements being axially elongate and having a center opening. A tie member connects opposed ends of adjacent elements. Adjacent annular units are interconnected at their tie members by a connecting member.

26 Claims, 13 Drawing Sheets

IMPLANTING STENT

This application is a divisional, of application Ser. No. 08/814,040, filed Mar. 10, 1997, now U.S. Pat. No. 5,879,381.

BACKGROUND OF THE INVENTION

1. Field of the Invention

This invention relates to an implanting stent useful in the treatment of any stricture in a body passageway such as blood vessel, bile duct, trachea, esophagus, and ureter.

2. Prior Art

Stents are generally tubular shaped devices which function to maintain open a segment of a blood vessel or other anatomical lumen. They are useful in the treatment of stenosis in blood vessels or other narrowed passageways.

In terms of their function and implantation, stents are generally classified into self-expandable stents and balloon expandable stents. The balloon expandable stent which itself has no expanding function is secured at a desired intralumenal location by mounting the stent on a balloon, delivering the stent to the desired location, and inflating the balloon so that the stent is expanded through plastic deformation by the dilating force of the balloon until it comes in close contact with the inner surface of the desired location. Stents of this type require the operation of expanding the stent as mentioned above.

With respect to balloon expandable stents, reference is made to Palmaz, U.S. Pat. Nos. 4,733,665 and 4,776,337 and Schatz, U.S. Pat. No. 5,195,984, which are incorporated herein by reference. These stents are pipes having axial slots formed therein. The slots are arranged such that they may take inter-connected rhombus shapes when the stent is expanded.

The expandable intralumenal graft or stent of U.S. Pat. Nos. 4,733,665 and 4,776,337 is improved in shape retention after expansion because slots take interconnected rhombus shapes. That is, the stent is resistant to the contracting force of a blood vessel. Another advantage is that when it is desired to partially enlarge the expanded diameter, an additional balloon corresponding to the enlarged diameter may be inserted inside the stent. Since the stent in an unexpanded state is a pipe having axial slots formed therein as viewed in side elevation, the stent lacks flexibility in an axial direction so that when the stent is to be inserted to the lesion, it is sometimes difficult to deliver the stent along a winding blood vessel. Additionally, when expanded, the stent is substantially reduced in overall length, leaving possibilities that the stenosis in a blood vessel is not dilated over its entirety and that the actual position of the stent is offset from the intended location under radiographic observation. In either case, effective treatment of stenosis is not expectable.

SUMMARY OF THE INVENTION

Therefore, an object of the present invention is to provide a stent which is improved in shape retention after expansion, smoothly passed through a winding passageway, and maintains its overall length substantially unchanged after expansion. Another object of the present invention is to provide such a stent which can dilate a stenosis in a blood vessel over its entirety and be accurately positioned at the desired location so that the stent is effective for the treatment of stenosis.

According to the invention, there is provided an implanting stent in the form of a generally tubular member having an axis and having a diameter allowing for insertion into a body passageway and radially expandable upon application of a radially outward extending force from the interior of the tubular member. The stent is constructed as a series of annular units arranged in an axial direction of the stent. Each annular unit includes a plurality of generally ellipsoidal or polygonal elements or cell members arranged so as to surround the stent axis, the elements being elongate in an axial direction of the stent and having a center opening, and a corresponding plurality of tie members each connecting circumferentially opposed ends of adjacent elements. Adjacent annular units are interconnected at their tie members by at least one connecting member.

DESCRIPTION OF THE PREFERRED EMBODIMENTS

Referring to FIGS. 1 to 7, a stent according to a first embodiment of the invention is described.

The stent generally designated at 1 according to the invention is a so-called balloon expandable stent in the form of a generally tubular member having a diameter allowing for insertion into a body passageway and radially expandable upon application of a radially outward extending force from the interior of the tubular member. The stent 1 has a center axis (not shown) extending in a horizontal direction as viewed in FIG. 1.

Figure 1:
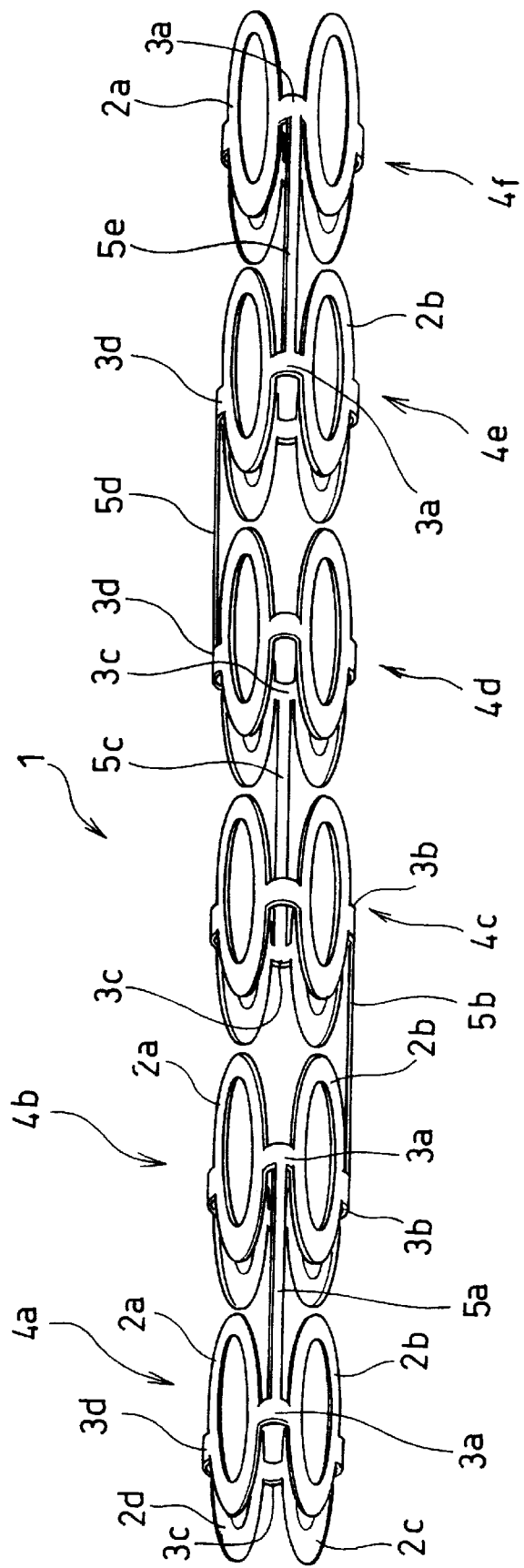
FIG. 1 is a perspective view of a stent according to one embodiment of the invention.
Figure 2:
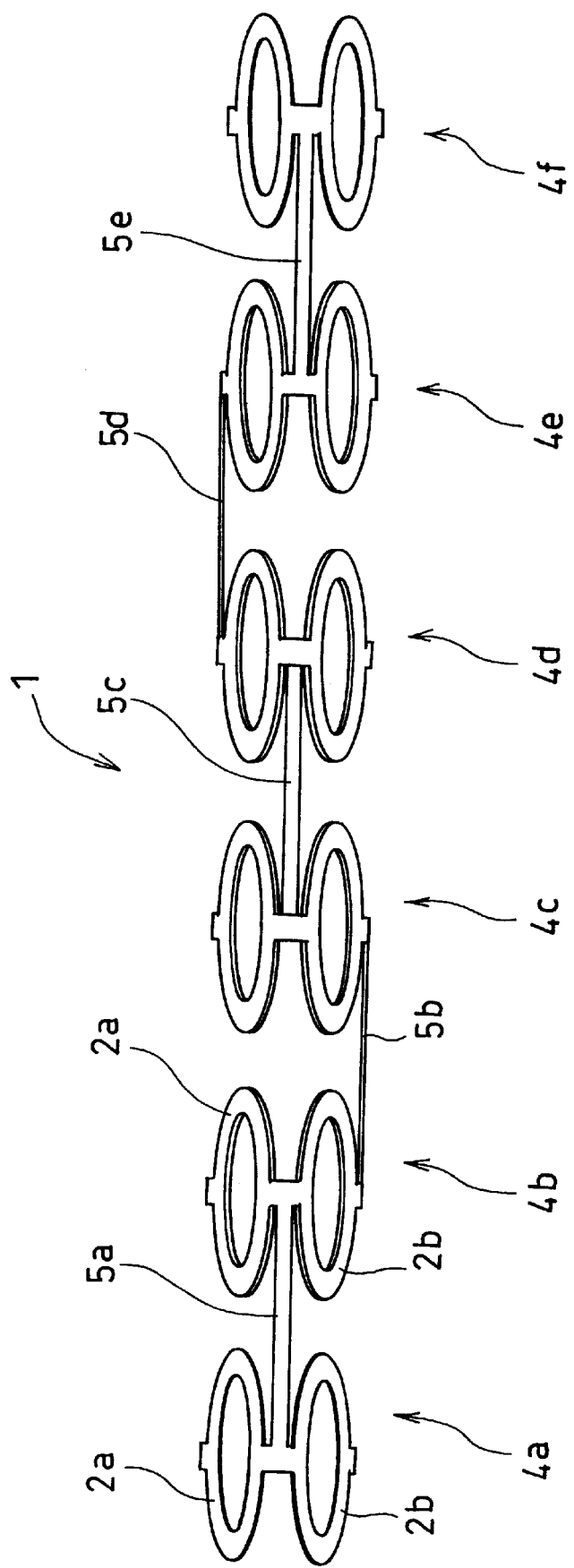
FIG. 2 is an elevational view of the stent of FIG. 1.
Figure 3:
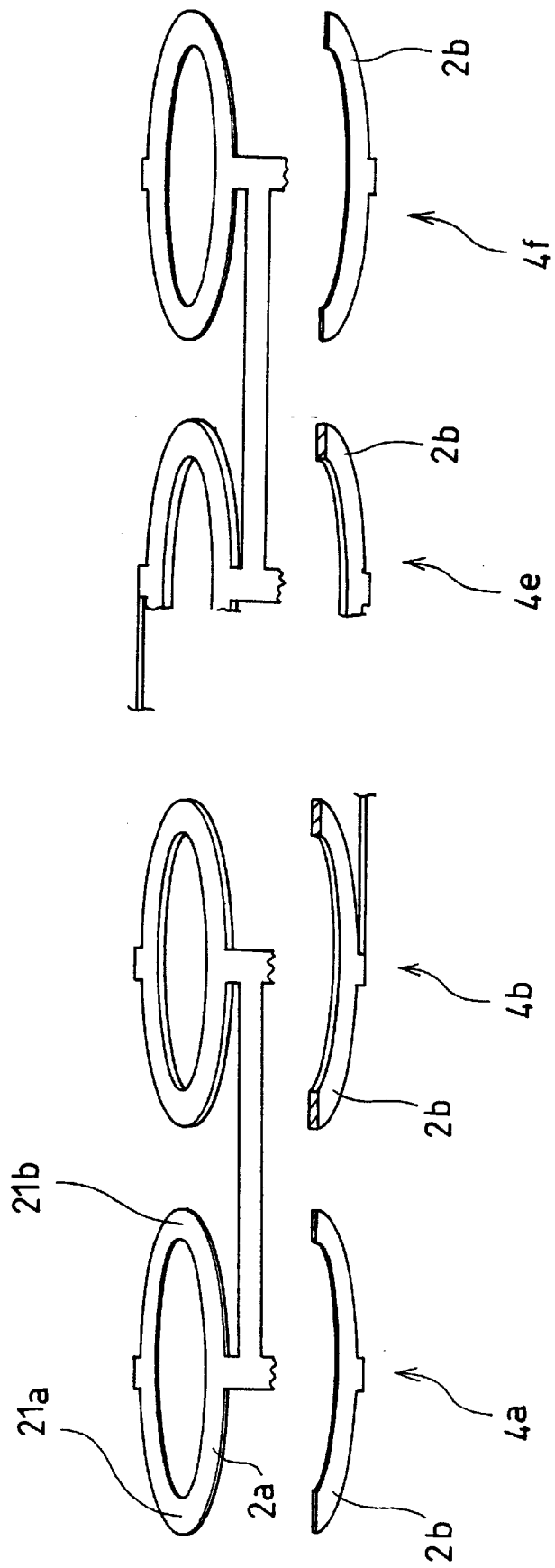
FIG. 3 is a partially cut-away fragmental view of the stent of FIG. 1.
Figure 4:
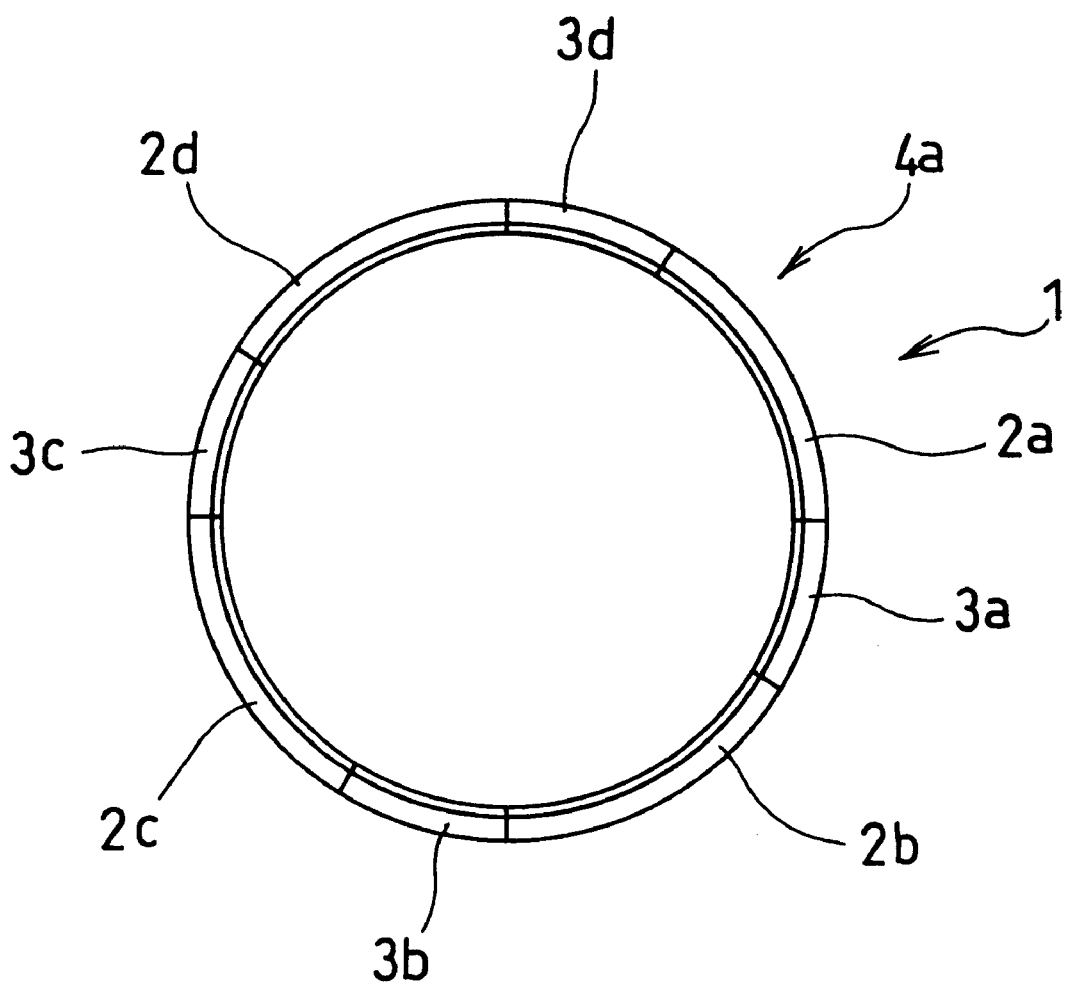
FIG. 4 is an end view of the stent of FIG. 1.
Figure 5:
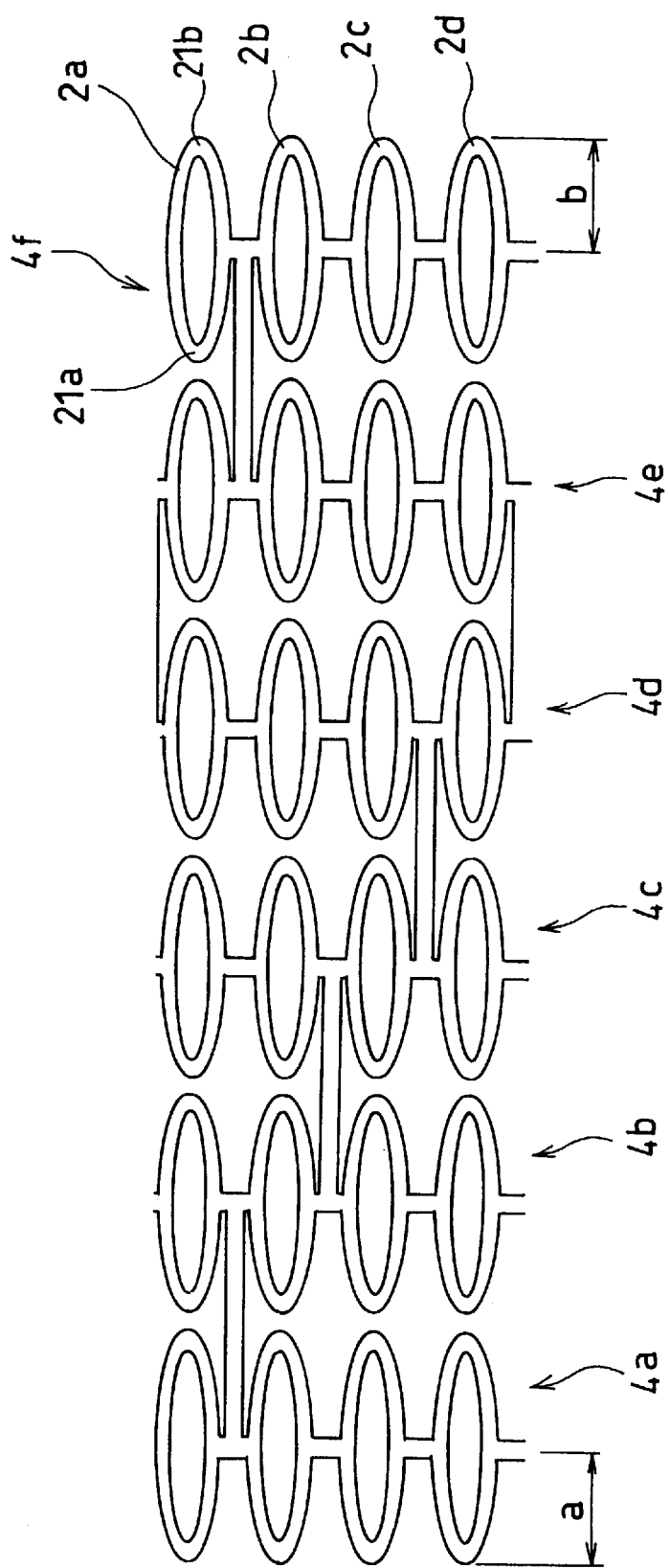
FIG. 5 is a development view of the stent of FIG. 1 before expansion.

As shown in FIGS. 1 to 3, the stent 1 includes a series of annular units 4 (4a, 4b, 4c, 4d, 4e, 4f) arranged in an axial direction of the stent. Each annular unit 4 includes a plurality of generally ellipsoidal or polygonal elements or cell members 2 which are elongate in an axial direction of the stent and have a center opening. The elements 2 are arranged so as to surround the stent axis. A corresponding plurality of tie members 3 (3a, 3b, 3c, 3d) each connect circumferentially opposed ends of adjacent elements 2. Adjacent annular units 4 (4a, 4b, 4c, 4d, 4e, 4f) are interconnected at their tie members 3 by at least one connecting member 5 (5a, 5b, 5c, 5d, 5e).

Differently stated, the stent 1 is a tubular shaped member comprising a series of annular units 4 interconnected by connecting members 5.

Since all the annular units are substantially the same, only one annular unit is described hereinafter. In the illustrated embodiment, the annular unit 4 includes four elements 2a, 2b, 2c and 2d arranged equiangularly with respect to the center axis of the stent. Each element 2 has a generally ellipsoidal shape elongated in an axial direction of the stent 1 and is formed at the center with a generally ellipsoidal opening conforming to the shape of the element. Each element 2 is configured as an independent closed cell. Differently stated, each element 2 is a ring which opens at the side surface of the stent 1. The elements of such configuration exert a strong force capable of retaining expansion. As best shown in the end view of FIG. 4, the elements 2a, 2b, 2c and 2d are curved so as to define a circle as a whole so that the elements are everywhere equally spaced from the center axis of the stent 1 or annular unit 4.

Circumferentially opposed ends of adjacent elements 2 are connected by tie members 3. One element 2 at the center of its one axial side is connected to a circumferentially adjacent element at the center of its one axial side by a short tie member 3. That is, tie members 3a, 3b, 3c, 3d connect the elements 2a, 2b, 2c and 2d in a circumferential direction to form one annular unit 4. Since the tie members 3 remain substantially unchanged even when the stent 1 is expanded, the expanding force acts on each element at its center so that the elements may be uniformly expanded or deformed.

The number of elements is not limited to four and may range from 3 to 8. The shape of elements is preferably generally ellipsoidal although the elements may be polygonal, for example, rhombic, axially elongated rectangular, hexagonal, and octagonal shapes. An ellipsoidal shape is most preferred because ellipsoidal elements undergo consistent deformation upon expansion of the stent.

The tie member 3 of one annular unit 4 is connected to the tie member 3 of an adjacent annular unit 4 by the connecting member 5 which is relatively long (that is, longer than the tie members) and extends parallel to the stent axis. More particularly, a first annular unit 4a is connected to an adjacent second annular unit 4b by a connecting member 5a extending between tie members 3a and 3a; the second annular unit 4b is connected to an adjacent third annular unit 4c by a connecting member 5b extending between tie members 3b and 3b; the third annular unit 4c is connected to an adjacent fourth annular unit 4d by a connecting member 5c extending between tie members 3c and 3c; the fourth annular unit 4d is connected to an adjacent fifth annular unit 4e by a connecting member 5d extending between tie members 3d and 3d; and the fifth annular unit 4e is connected to an adjacent sixth annular unit 4f by a connecting member 5e extending between tie members 3a and 3a.

These connecting members 5a, 5b, 5c, 5d and 5e remain substantially unchanged even when the stent 1 is expanded. Since the tie members 3 and the connecting members 5 remain substantially unchanged even when the stent 1 is expanded, the overall length of the stent 1 remains substantially unchanged before and after expansion. It never happens that the stent is extremely reduced in length after expansion. Differently stated, the overall length of the stent 1 is not substantially reduced upon expansion since the tie members 3 tying expandable elements are not axially moved upon expansion of the stent and the tie members 3 are connected to each other by the axially extending connecting members 5.

In the illustrated embodiment, the connecting member 5 connects adjacent annular units 4 at only one position. Although adjacent annular units 4 may be connected at two or more positions (typically using two or more connecting members), connection at only one position as in the illustrated embodiment is preferred in order that the stent faithfully follow deformation of a blood vessel. Further in the illustrated embodiment, one connecting member 5 is axially offset from an adjacent connecting member 5. That is, one connecting member 5 is not continuous to an adjacent connecting member 5. The offsetting of connecting members 5 prevents the load appearing upon deformation of one annular unit 4 to follow deformation of a blood vessel from being directly or linearly transmitted to non-adjacent annular units, allowing the respective annular units to independently exert their expansion function. Further in the illustrated embodiment, a series of connecting members 5a, 5b, 5c, 5d and 5e are successively helically spaced apart as viewed from the entire stent, minimizing potential interaction between non-adjacent annular units.

The ellipsoidal elements 2 are axially aligned among the series of annular units 4. The elements 2 of the respective annular units 4 are arranged in a substantially linear array in an axial direction of the stent 1. All the connecting members 5 extend parallel to the stent axis. This prevents the connecting members 5 from being twisted. All the tie members 3 extend transverse to the stent axis. This prevents the tie members 3 from being twisted.

Upon expansion of the stent 1, the elements 2a, 2b, 2c and 2d deform such that axially opposed ends 21a and 21b may be spread or widened. To ensure spreading deformation and to ensure that such deformation occur at axially opposed ends of each element, the elements 2a, 2b, 2c and 2d are configured such that axially opposed ends 21a and 21b of the elements 2a, 2b, 2c and 2d have a smaller cross-sectional area than the remainder. More particularly, in the embodiment shown in FIG. 3, axially opposed ends 21a and 21b of the element 2 have a narrower width than the remainder. Alternatively, axially opposed ends 21a and 21b of the element 2 may have a less wall thickness than the remainder. It is understood that the element is an ellipsoidal band whose cross section has a width and a thickness.

The elements of those annular units 4a and 4f which are located at axially opposed ends of the stent 1 have a smaller cross-sectional area than the elements of the remaining annular units 4b, 4c, 4d and 4e as shown in FIG. 3. Then the expanding forces exerted at opposed ends of the stent upon expansion of the stent are smaller than at other regions, which means that the end annular units of the stent will more easily follow curve section of a blood vessel and have more affinity to the blood vessel. Since components of the stent are made of a metallic material, typically stainless steel as will be described later, one exemplary process to ensure that only those elements of the end annular units 4a and 4f have a less wall thickness involves chemical or mechanical polishing of the annular units 4a and 4f after the stent has been fabricated to the final shape. Chemical polishing is preferably carried out by dipping in a chemical polishing solution for stainless steel. Any chemical polishing solution containing an acid capable of dissolving stainless steel may be used. For example, one preferred chemical polishing solution contains a mixture of hydrochloric acid and nitric acid as a base component and additives such as organic sulfur compounds and surfactants for adjusting a dissolution rate, smoothing and imparting luster. The cross-sectional area reducing means is not limited thereto and the elements of annular units are formed such that those elements of end annular units 4a and 4f have a narrower width than the elements of the remaining annular units 4b, 4c, 4d and 4e.

In another preferred embodiment, the members of the annular unit located at the center of the stent 1 have the maximum cross-sectional area and the cross-sectional area of members of annular units is reduced as the unit is located nearer to the end of the stent. Specifically, the members of the annular unit located at the center of the stent 1 have the maximum wall thickness and the wall thickness of members of annular units is reduced as the unit is located nearer to the end of the stent. More specifically, the members of the annular units 4c and 4d located at the center of the stent 1 have the maximum wall thickness, the members of adjacent annular units 4b and 4e have a less wall thickness, and the members of end annular units 4a and 4f have a less wall thickness than that of annular units 4b and 4e. The progressive wall thickness reduction from the center to the end ensures that the stent exerts a sufficient expanding force at the center and that opposite ends of the stent faithfully follow a winding blood vessel and have better affinity thereto. Alternatively, it is acceptable that the members of the annular unit located at the center of the stent 1 have the maximum width and the width of members of annular units is reduced as the unit is located nearer to the end of the stent.

The members of the stent 1 are made of a material having a certain degree of biological compatibility. For example, stainless steel, tantalum and tantalum alloys, platinum and platinum alloys, gold and gold alloys, and cobalt base alloys are useful. It is also acceptable to plate a stent with a noble metal such as gold and platinum after the stent has been fabricated into a final shape. Preferred stainless steel is SUS 316L featuring maximum corrosion resistance.

After the stent has been fabricated from a metallic material into a final shape, annealing is preferably carried out. Annealing improves the flexibility and plasticity of the overall stent so that the stent may be more effectively implanted in a winding section of blood vessel. As compared with a non-annealed stent, the annealed stent when expanded from an original shape to an expanded shape has a reduced force of restoring to the original shape, and especially when expanded at a curved section of blood vessel, has a reduced force of restoring to be straight. This minimizes physical stimulation to the inner wall of the curved blood vessel, reducing the cause of stenosis recurrence. The stent is preferably annealed by heating it to 900 to 1200° C. in an inert gas atmosphere (e.g., argon gas) and then slowly cooling so that no oxide coating may be formed on the stent surface.

With respect to preferred dimensions, the stent 1 in an unexpanded state preferably has a diameter of about 1.2 to 1.8 mm, especially about 1.3 to 1.6 mm. One annular unit 4 and hence, one element 2 has an axial length of about 1.5 to 4.0 mm, especially about 2.0 to 3.0 mm. The number of annular units is 3 to 10. The annular unit(s) at the center of the stent is constructed by members having a thickness of about 0.05 to 0.12 mm, especially 0.06 to 0.10 mm while the annular units at opposite ends of the stent are constructed by members having a thickness of about 0.05 to 0.07 mm. The thickness of members of end annular units is about ⅗ to ⅘ of the thickness of members of center annular units.

Figure 8:
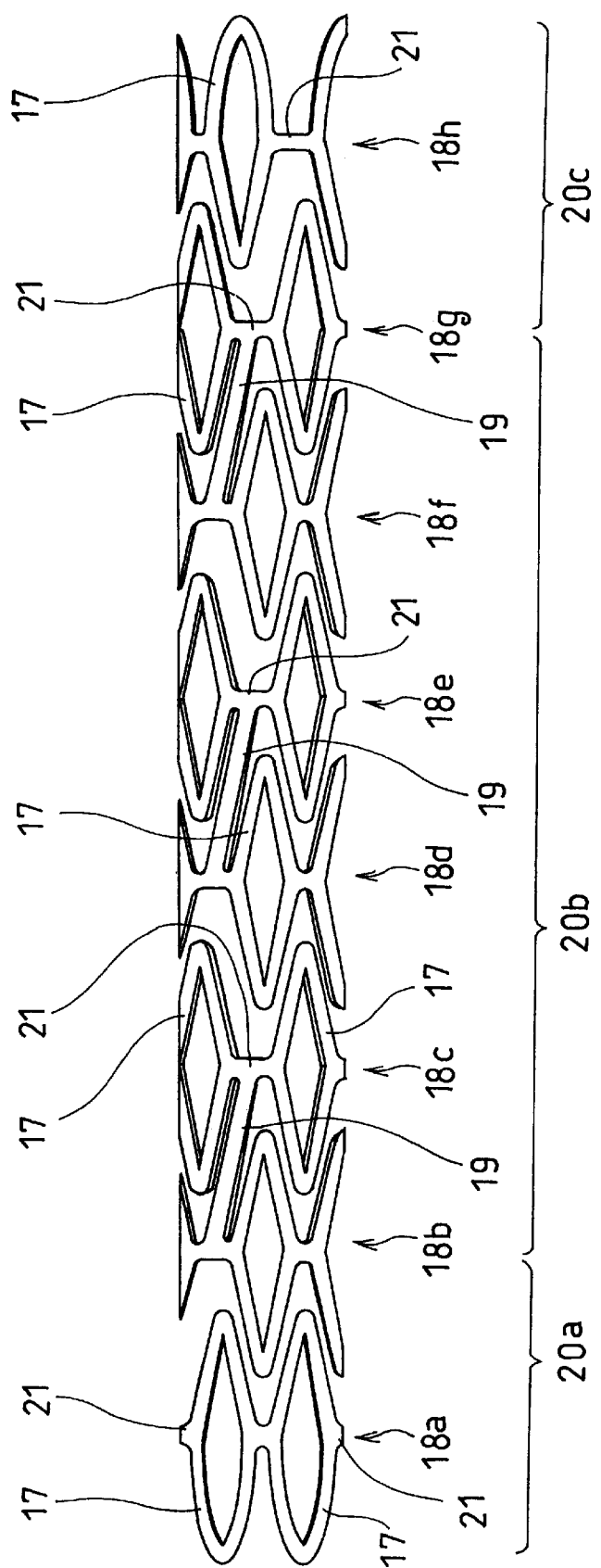
FIG. 8 is an elevational view of a stent according to another embodiment of the invention.
Figure 9:
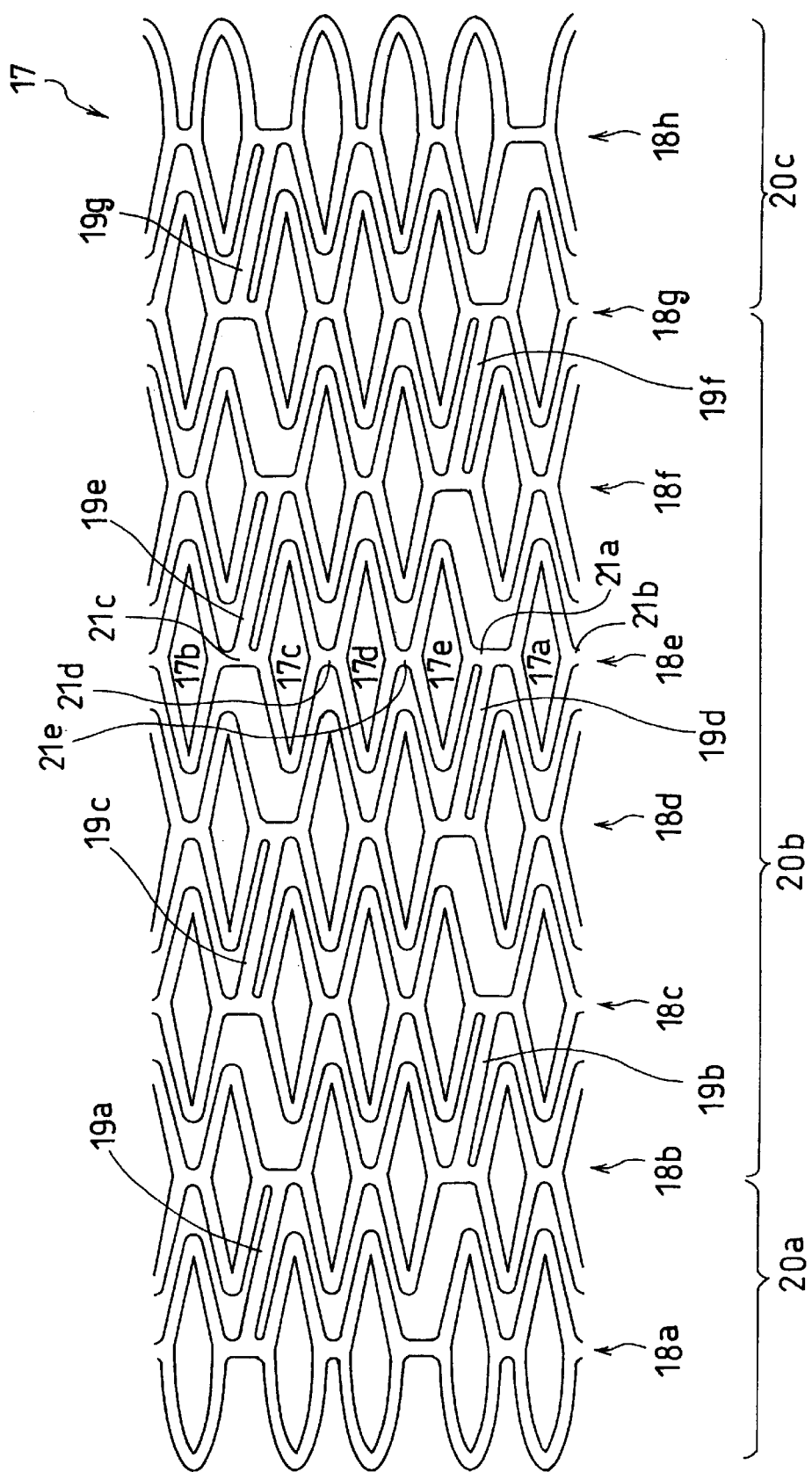
FIG. 9 is a development view of the stent of FIG. 8 before expansion.
Figure 10:
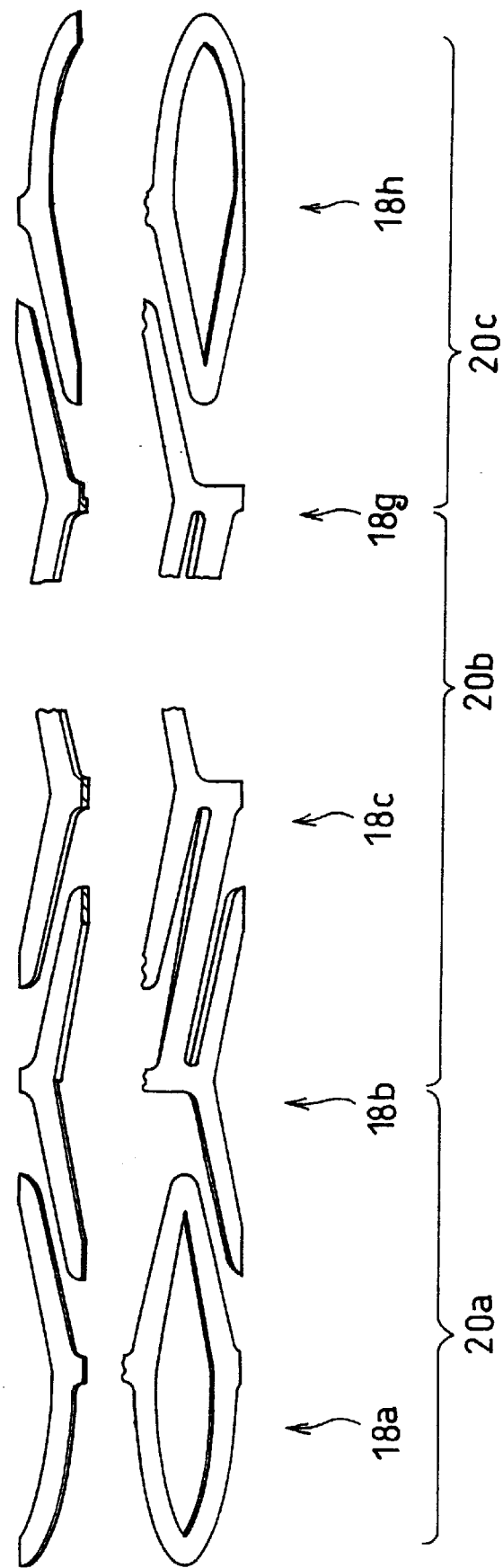
FIG. 10 is a partially cut-away fragmental view of the stent of FIG. 8.

Referring to FIGS. 8 to 10, there is illustrated a stent according to a second embodiment of the invention. The stent 20 of this embodiment has the same basic construction as the stent 1 of the first embodiment.

As shown in FIGS. 8 and 9, the stent 20 having an axis includes a series of annular units 18 (18a, 18b, 18c, 18d, 18e, 18f, 18g, 18h) arranged in an axial direction of the stent. Each annular unit 18 includes a plurality of generally ellipsoidal or polygonal elements 17 (17a, 17b, 17c, 17d, 17e) which are elongate in an axial direction of the stent and have a center opening. The elements 17 are arranged so as to surround the stent axis. A corresponding plurality of tie members 21 (21a, 21b, 21c, 21d, 21e) each connect circumferentially opposed ends of adjacent elements 17. Adjacent annular units 18 (18a, 18b, 18c, 18d, 18e, 18f, 18g, 18h) are interconnected at their tie members 21 by one connecting member 19 (19a, 19b, 19c, 19d, 19e, 19f, 19g).

In the stent 20, two adjacent elements 17 of one annular unit 18 and the tie member 21 connecting them define therebetween a space into which an axial end of an element 17 of an adjacent annular unit 18 extends. Then the annular units are partially overlapped in an axial direction of the stent. With such overlapping arrangement of annular units, even when the individual elements are reduced in axial length upon expansion of the stent 20, gaps on the side surface of the stent 20 are less increased, ensuring that the stenosis in a blood vessel is dilated and held dilated.

As in the first embodiment, the stent 20 is a tubular shaped member comprising a series of annular units 18 interconnected by connecting members 19.

In the illustrated embodiment, the annular unit 18 includes five elements 17a, 17b, 17c, 17d and 17e arranged equiangularly with respect to the center axis of the stent. Each element 17 has a generally rhombic shape elongated in an axial direction of the stent 20 and is formed at the center with a generally rhombic opening conforming to the shape of the element. The elements of the annular units at axially opposed ends of the stent 20 have a generally semi-ellipsoidal shape at their outer half in order to have a sufficient expanding force at the stent ends and to minimize injury to the inner wall of a blood vessel (where the stent is implanted) and the balloon. The elements 17a, 17b, 17c, 17d and 17e are curved so as to define a circle as a whole (as viewed in an end view similar to FIG. 4) so that the elements are everywhere equally spaced from the center axis of the stent 20 or annular unit 18.

Circumferentially opposed ends of adjacent elements 17 are connected by tie members 21. One element 17 at the center of its one axial side is connected to a circumferentially adjacent element at the center of its one axial side by a short tie member 21. In this embodiment, the elements 17 are divided into two groups, a first group of 17a and 17b and a second group of 17c, 17d and 17e. The elements in each group are tied to each other by a very short tie member 21 whereas an element in one group is tied to an element of the other group by a relatively long tie member 21. More specifically, elements 17a and 17b are tied by a very short tie member 21b, elements 17c and 17d are tied by a very short tie member 21d, and elements 17d and 17e are tied by a very short tie member 21e whereas elements 17e and 17a and elements 17b and 17c are tied by relatively long tie members 21a and 21c, respectively. Therefore, all the spacings between elements are not equal. The elements are formed to a generally rhombic shape because a relatively large space is defined between opposed sides of adjacent elements. That is, a generally V-shaped or trapezoidal space is defined between opposed sides of adjacent elements.

As shown in FIGS. 8 and 9, into the space defined between opposed sides of adjacent elements of one annular unit, an axial end of one element of an adjacent annular unit extends to reduce the gap formed on the side surface of the stent. In this way, one element of a first annular unit penetrates between adjacent elements of a second annular unit (to near the tie member) so that the elements are partially overlapped in an axial direction, enabling to arrange more annular units within the stent of a predetermined length. In the illustrated embodiment, eight annular units are axially connected to construct a stent.

The relatively long tie member 21a of one annular unit 18a is connected to the relatively long tie member 21b of an adjacent annular unit 18b by a relatively long (longer than the tie member), axially extending connecting member 19a. In the illustrated embodiment, the connecting member 19 is inclined at an angle of about 12° with respect to the stent axis. Generally stated, when the stent 20 is longitudinally cut parallel to the stent axis and developed flat as shown in the development view of FIG. 9, the connecting members 19 are inclined at an angle with respect to a longitudinal direction of the stent and parallel to each other.

Also in the stent 20 of this embodiment, the connecting member 19 connects adjacent annular units 18 at only one position. Further in the illustrated embodiment, one connecting member 19 is axially offset from an adjacent connecting member 19. That is, one connecting member 19 is not continuous to an adjacent connecting member 19. The offsetting of connecting members 19 prevents the load appearing upon deformation of one annular unit 18 to follow deformation of a blood vessel from being directly or linearly transmitted to non-adjacent annular units, allowing the respective annular units to independently exert their expansion function. Further in the illustrated embodiment, a series of connecting members 19 are helically spaced apart as viewed from the entire stent (that is, sparse positioning in helical turns in the figure). Since all the connecting members are parallel to each other, the stent is less twisted upon expansion.

Upon expansion of the stent 20, the elements 17a, 17b, 17c, 17d and 17e deform such that axially opposed ends thereof may be spread or widened. To ensure spreading deformation and to ensure that such deformation occur at axially opposed ends of each element, the elements 17a, 17b, 17c, 17d and 17e are configured such that axially opposed ends of the elements have a smaller cross-sectional area than the remainder. Moreover, members in axially opposed end regions 20a and 20c of the stent 20 have a smaller cross-sectional area than members in an intermediate region 20b as shown in FIG. 10. Then the expanding forces exerted at opposed end regions of the stent upon expansion of the stent are smaller than at the intermediate region, which means that the end annular units of the stent will more easily follow curve section of a blood vessel and have more affinity to the blood vessel. More specifically, members in the end regions 20a and 20c of the stent 20 have a less wall thickness than members in the intermediate region 20b. Alternatively, members in the end regions 20a and 20c of the stent 20 may have a less width than members in the intermediate region 20b.

With respect to preferred dimensions, the stent 20 in an unexpanded state has a diameter of about 1.2 to 1.8 mm, especially about 1.3 to 1.6 mm. One annular unit 18 and hence, one element 17 has an axial length of about 1.5 to 4.0 mm, especially about 2.0 to 3.0 mm. The number of annular units is 6 to 10. The elements of adjacent annular units have an axial overlap of about 0.5 to 1 mm. The center-to-center distance between the elements of one annular unit and the elements of an adjacent annular unit is about 1.3 to 2.5 mm. The connecting members have a length of 1.4 to 2.7 mm. The angle of inclination of connecting members relative to the stent axis (that is, the angle of inclination of connecting members relative to a longitudinal direction in a development view) is about 0° to 30°, especially 5° to 25°. The annular units in the intermediate region of the stent are constructed by members having a thickness of about 0.05 to 0.12 mm, especially 0.06 to 0.10 mm while the annular units in the end regions of the stent are constructed by members having a thickness of about 0.05 to 0.07 mm. The thickness of members of end annular units is preferably about ⅗ to ⅘ of the thickness of members of intervening annular units.

With respect to other parameters, for example, stent forming material, the same as in the first embodiment applies.

Figure 12:
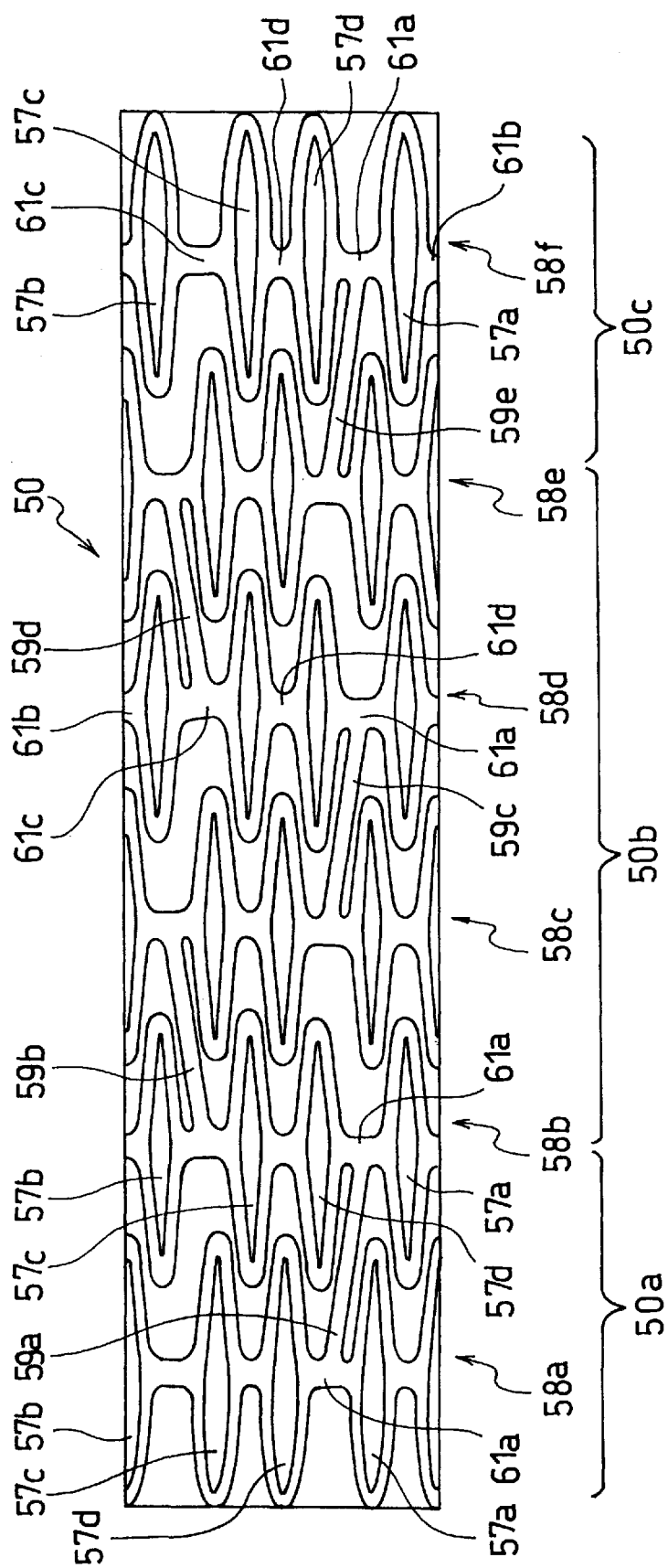
FIG. 12 is a development view of a stent according to another embodiment of the invention before expansion.

Referring to FIG. 12, there is illustrated a stent according to a third embodiment of the invention. The stent 50 of this embodiment has the same basic construction as the stent 1 of the first embodiment.

As shown in FIG. 12, the stent 50 having an axis includes a series of annular units 58 (58a, 58b, 58c, 58d, 58e, 58f) arranged in an axial direction of the stent. Each annular unit 58 includes a plurality of generally ellipsoidal or polygonal elements 57 (57a, 57b, 57c, 57d) which are elongate in an axial direction of the stent and have a center opening. The elements 57 are arranged so as to surround the stent axis. A corresponding plurality of tie members 61 (61a, 61b, 61c, 61d) each connect circumferentially opposed ends of adjacent elements 57. Adjacent annular units 58 (58a, 58b, 58c, 58d, 58e, 58f) are interconnected at their tie members 61 by one connecting member 59 (59a, 59b, 59c, 59d, 59e).

In the stent 50, two adjacent elements 57 of one annular unit 58 and the tie member 61 connecting them define therebetween a space into which an axial end of an element 57 of an adjacent annular unit 58 extends. Then the annular units are partially overlapped in an axial direction of the stent. With such overlapping arrangement of annular units, even when the individual elements are reduced in axial length upon expansion of the stent 50, gaps on the side surface of the stent 50 are less increased, ensuring that the stenosis in a blood vessel is dilated and held dilated.

As in the first embodiment, the stent 50 is a tubular shaped member comprising a series of annular units 58 interconnected by connecting members 59.

In the illustrated embodiment, the annular unit 58 includes four elements 57a, 57b, 57c and 57d arranged equiangularly with respect to the center axis of the stent. Each element 57 has a generally rhombic shape elongated in an axial direction of the stent 50 and is formed at the center with a generally rhombic opening conforming to the shape of the element. The elements of the annular units at axially opposed ends of the stent 50 have a generally semi-ellipsoidal shape at their outer half in order to have a sufficient expanding force at the stent ends and to minimize injury to the inner wall of a blood vessel (where the stent is implanted) and the balloon. The elements 57a, 57b, 57c, 57d and 57e are curved so as to define a circle as a whole (as viewed in an end view similar to FIG. 4) so that the elements are everywhere equally spaced from the center axis of the stent 50 or annular unit 58.

Circumferentially opposed ends of adjacent elements 57 are connected by tie members 61. One element 57 at the center of its one axial side is connected to a circumferentially adjacent element at the center of its one axial side by a short tie member 61. In this embodiment, the elements 57 are divided into two groups, a first group of 57a and 57b and a second group of 57c and 57d. The elements in each group are tied to each other by a very short tie member 61 whereas an element in one group is tied to an element of the other group by a relatively long tie member 61. More specifically, elements 57a and 57b are tied by a very short tie member 61b, and elements 57c and 57d are tied by a very short tie member 61d whereas elements 57d and 57a and elements 57b and 57c are tied by relatively long tie members 61a and 61c, respectively. Therefore, all the spacings between elements are not equal. The elements are formed to a generally rhombic shape because a relatively large space is defined between opposed sides of adjacent elements. That is, a generally V-shaped or trapezoidal space is defined between opposed sides of adjacent elements.

As shown in FIG, 12, into the space defined between opposed sides of adjacent elements of one annular unit, an axial end of one element of an adjacent annular unit extends to reduce the gap formed on the side surface of the stent. In this way, one element of a first annular unit penetrates between adjacent elements of a second annular unit (to near the tie member) so that the elements are partially overlapped in an axial direction, enabling to arrange more annular units within the stent of a predetermined length. In the illustrated embodiment, six annular units are axially connected to construct a stent.

The relatively long tie member 61a of one annular unit 58a is connected to the relatively long tie member 61a of an adjacent annular unit 58b by a relatively long (longer than the tie member), axially extending connecting member 59a. In the illustrated embodiment, the connecting member 59 is inclined at an angle of about 12° with respect to the stent axis. Generally stated, when the stent 50 is longitudinally cut parallel to the stent axis and developed flat as shown in the development view of FIG. 12, the connecting members 59 are inclined at an angle with respect to a longitudinal direction of the stent. As shown in FIG. 12, the connecting members (59a, 59c and 59e) of the odd number location in the stent 50 are parallel to each other. The connecting members (59b, 59d) of even number location in the stent 50 are parallel to each other. But the connecting members (59a, 59c and 59e) of the odd number location in the stent 50 are not parallel the connecting members (59b, 59d) of even number location in the stent 50. A series of connecting members (59a, 59c and 59e) of the odd number location in the stent 50 are helically spaced apart as viewed from the entire stent. A series of connecting members (59b, 59d) of even number location in the stent 50 are helically spaced apart as viewed from the entire stent.

Also in the stent 50 of this embodiment, the connecting member 59 connects adjacent annular units 58 at only one position. Further in the illustrated embodiment, one connecting member 59 is axially offset from an adjacent connecting member 59. That is, one connecting member 59 is not continuous to an adjacent connecting member 59. The offsetting of connecting members 59 prevents the load appearing upon deformation of one annular unit 58 to follow deformation of a blood vessel from being directly or linearly transmitted to non-adjacent annular units, allowing the respective annular units to independently exert their expansion function. Further in the illustrated embodiment, a series of connecting members 59 does not continue each other.

Upon expansion of the stent 50, the elements 57a, 57b, 57c and 57d deform such that axially opposed ends thereof may be spread or widened. To ensure spreading deformation and to ensure that such deformation occur at axially opposed ends of each element, the elements 57a, 57b, 57 and 57d are configured such that axially opposed ends of the elements have a smaller cross-sectional area than the remainder. Moreover, members in axially opposed end regions 50a and 50c of the stent 50 may have a smaller cross-sectional area than members in an intermediate region 50b. Then the expanding forces exerted at opposed end regions of the stent upon expansion of the stent are smaller than at the intermediate region, which means that the end annular units of the stent will more easily follow curve section of a blood vessel and have more affinity to the blood vessel. More specifically, members in the end regions 50a and 50c of the stent 50 have a less wall thickness than members in the intermediate region 50b. Alternatively, members in the end regions 50a and 50c of the stent 50 may have a less width than members in the intermediate region 50b.

With respect to preferred dimensions, the stent 50 in an unexpanded state has a diameter of about 1.2 to 1.8 mm, especially about 1.3 to 1.6 mm. One annular unit 58 and hence, one element 57 has an axial length of about 1.5 to 4.0 mm, especially about 2.0 to 3.0 mm. The number of annular units is 5 to 15. The elements of adjacent annular units have an axial overlap of about 0.2 to 1.05 mm. The center-to-center distance between the elements of one annular unit and the elements of an adjacent annular unit is about 2.5 to 4.0 mm. The connecting members have a length of 2.6 to 5.0 mm. The angle of inclination of connecting members relative to the stent axis (that is, the angle of inclination of connecting members relative to a longitudinal direction in a development view) is about 0° to 30°, especially 5° to 25°. The annular units in the intermediate region of the stent are constructed by members having a thickness of about 0.05 to 0.12 mm, especially 0.06 to 0.10 mm while the annular units in the end regions of the stent are constructed by members having a thickness of about 0.05 to 0.07 mm. The thickness of members of end annular units is preferably about ⅗ to ⅘ of the thickness of members of intervening annular units.

With respect to other parameters, for example, stent forming material, the same as in the first embodiment applies.

Although the stent of the invention has been described as being applied to dilate stenosis in a blood vessel, the stent may be equally applicable to improve stenosis in any body passageway such as bile duct, trachea, esophagus, and ureter. The size of the stent and elements may be determined in accordance with a particular body passageway into which the stent is implanted.

Figure 6:
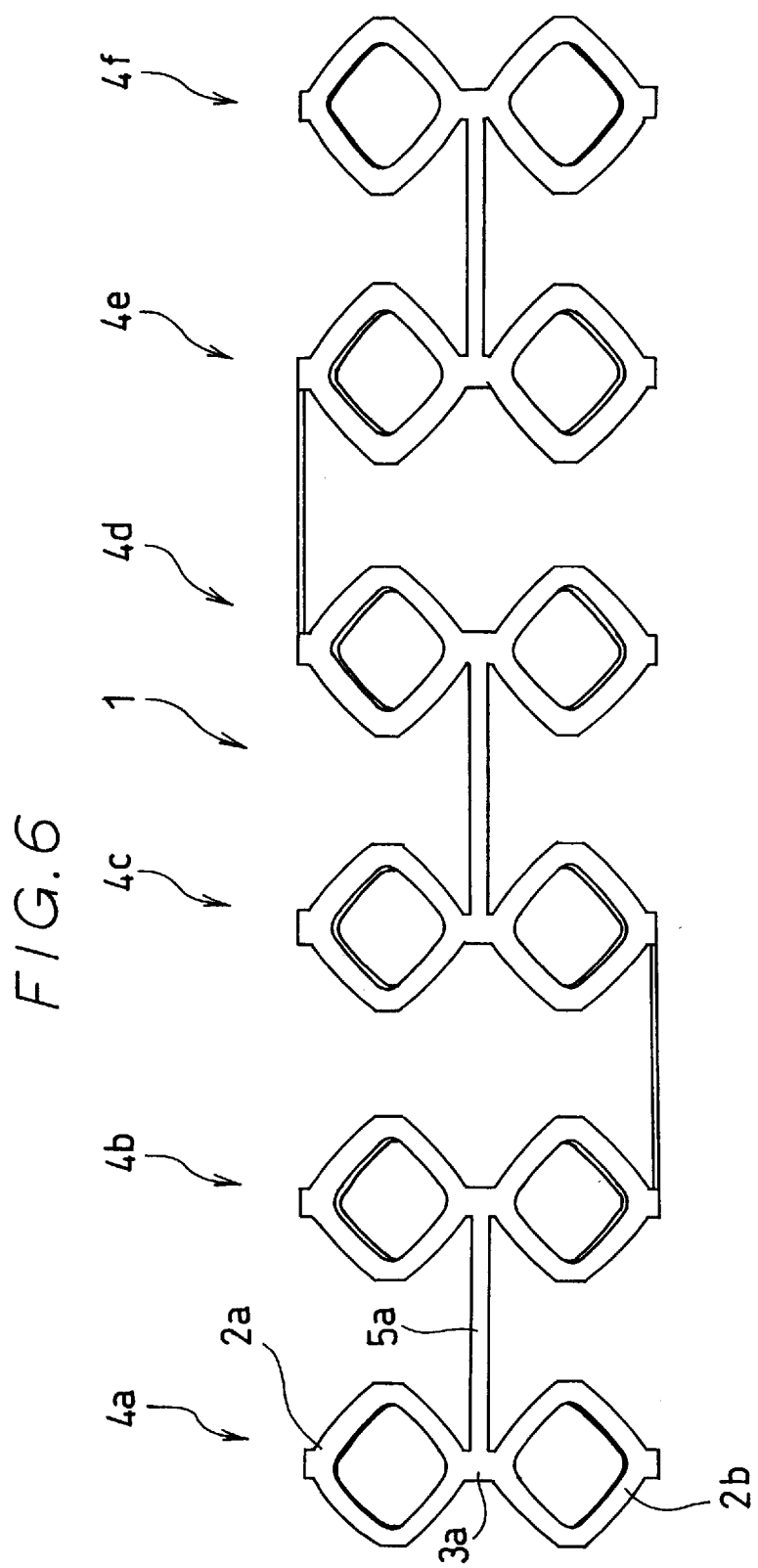
FIG. 6 is an elevational view of the expanded stent of FIG. 1.
Figure 7:
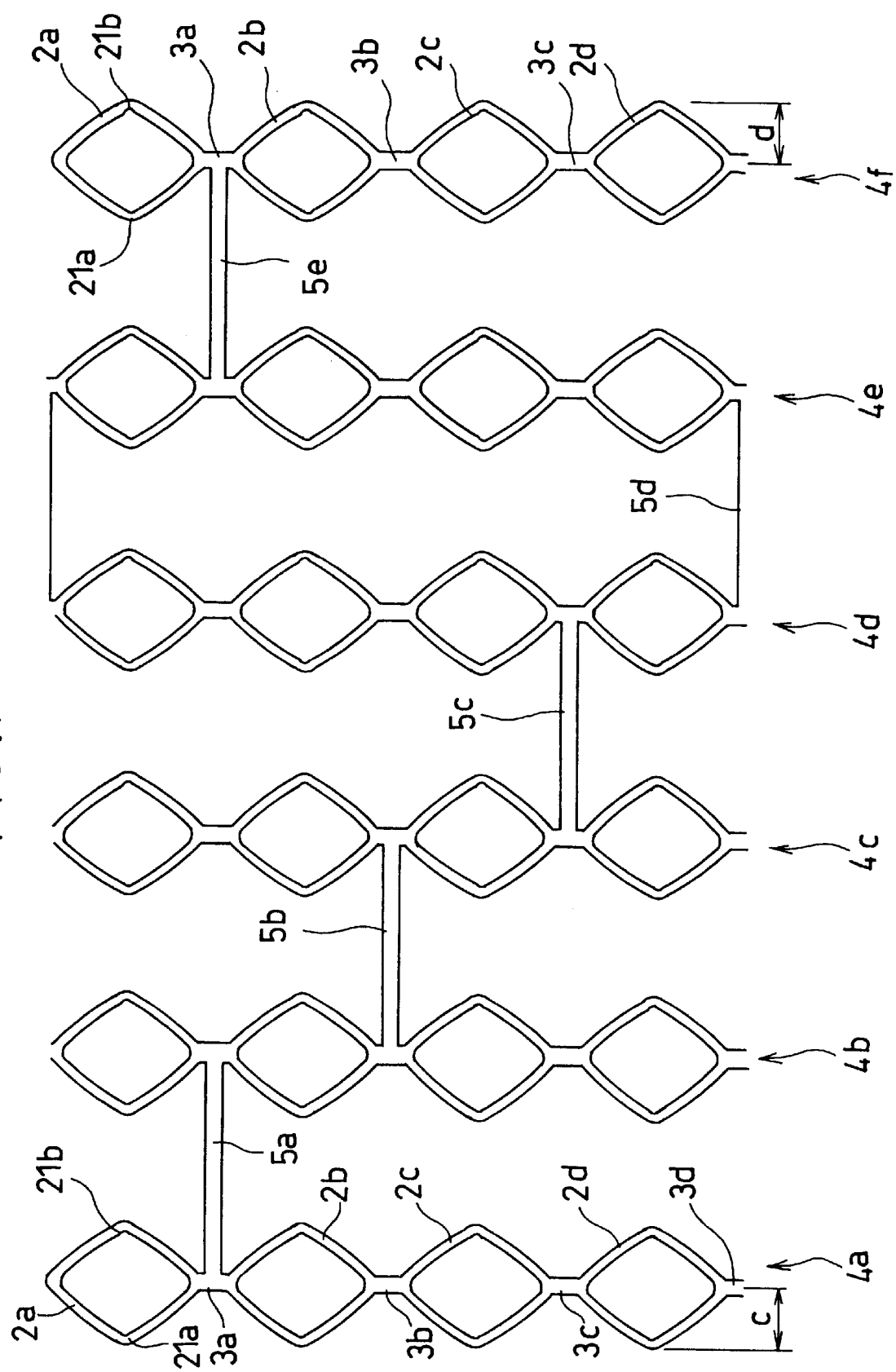
FIG. 7 is a development view of the expanded stent of FIG. 1.
Figure 11:
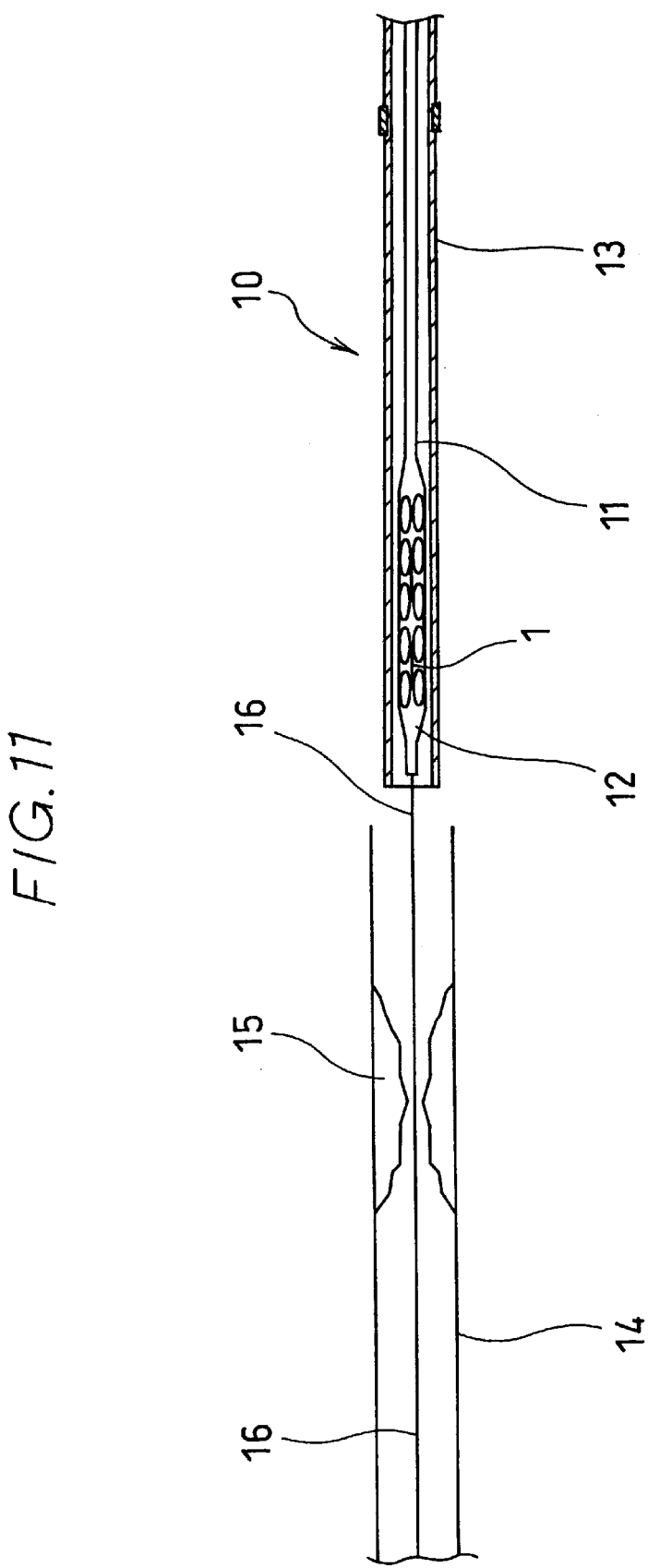
FIG. 11 illustrates the manner of inserting the stent.

Next, the operation of the stent according to the invention is described in conjunction with FIGS. 6, 7, and 11.

A stent delivery device 10 includes a stent 1, a balloon catheter 11 for expanding the stent in a section of blood vessel, and a protective sheath 13 having the catheter 11 received therein. The balloon catheter 11 has a folded balloon 12 on which the stent 1 is mounted. When the stent is delivered to a desired location, the delivery device is advanced through a narrow and winding blood vessel with the stent 1 retracted within the protective sheath 13 because the stent would otherwise be detached by friction with the blood vessel.

The stent delivery device 10 is advanced through a blood vessel 14 by inserting a guide wire 16 through the balloon catheter 11, passing only the guide wire 16 into a stenosis 15 in the blood vessel, and thereafter advancing the stent delivery device 10 along the guide wire 16. After the stent deliver device 10 together with the sheath 13 is advanced into the stenosis 15, it is confirmed by radiographic observation that the distal end of the sheath has reached within the stenosis 15. At this position, only the sheath 13 is moved back. A radiographic contrast medium is injected into the balloon 12 under high pressure to inflate the balloon. As the balloon 12 is inflated, the stent 1 is expanded through plastic deformation so that its radius is radially enlarged, thereby dilating the stenosis 15. Thereafter, the fluid pressure is released to allow the balloon to contract. At this point, the stent does not contract by virtue of the expansion or shape retaining force due to plastic deformation, remains at the expanded position and maintains the blood vessel dilated, improving blood flow disturbance.

When the balloon applies an expanding force to the stent, the stent receives a radially outward spreading force. Since the tie members tie sides of ellipsoidal elements at the center, the spreading force acts to pull the element at the tying tie members in opposite directions whereby the ellipsoidal elements are regularly deformed into a generally rhombic shape as shown in FIGS. 6 and 7. Upon expansion, the respective elements are individually reduced in axial length. Since such axial shortening is very slight, the overall length of the stent is little shortened.

Figure 13:
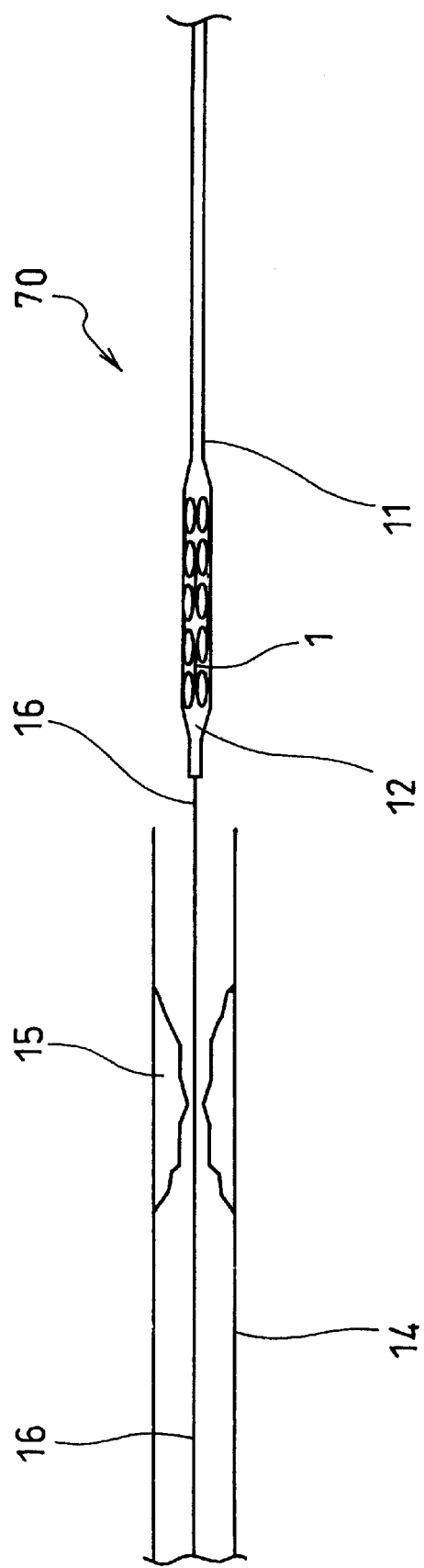
FIG. 13 illustrates the another manner of inserting the stent.

Next, the another operation of the stent according to the invention is described in conjunction with FIGS. 6, 7, and 13.

A stent delivery device 70 includes a stent 1, a balloon catheter 11 for expanding the stent in a section of blood vessel. The balloon catheter 11 has a folded balloon 12 on which the stent 1 is mounted.

The stent delivery device 70 is advanced through a blood vessel 14 by inserting a guide wire 16 through the balloon catheter 11, passing only the guide wire 16 into a stenosis 15 in the blood vessel, and thereafter advancing the stent delivery device 70 along the guide wire 16. After the stent deliver device 70 is advanced into the stenosis 15, it is confirmed by radiographic observation that the stent 1 has reached within the stenosis 15. A radiographic contrast medium is injected into the balloon 12 under high pressure to inflate the balloon. As the balloon 12 is inflated, the stent 1 is expanded through plastic deformation so that its radius is radially enlarged, thereby dilating the stenosis 15. Thereafter, the fluid pressure is released to allow the balloon to contract. At this point, the stent does not contract by virtue of the expansion or shape retaining force due to plastic deformation, remains at the expanded position and maintains the blood vessel dilated, improving blood flow disturbance.

EXAMPLE

Examples of the present invention are given below by way of illustration and not by way of limitation.

Example 1

A metal pipe of stainless steel SUS 316L having a diameter of 1.4 mm and a gage of 0.10 mm was cut to a length of 50 mm.

A stent was prepared by hollowing out a metal pipe to leave a stent skeleton. A stent skeleton can be hollowed out of a metal pipe in many ways. Exemplary processes include an etching process, known as photofabrication, using masks and chemicals, electric discharge machining, and mechanical machining. A laser machining process was used herein because it is most simple to operate and highest in precision.

A laser machining device used was a YAG laser model SL116E manufactured by NEC. The metal pipe was mounted on a jig equipped with a rotating motor by means of a chuck mechanism such that the pipe might be kept aligned. The jig was set on a numerically controlled XY table. The XY table and the rotating motor were connected to a personal computer such that an output of the computer was delivered to a numerical controller of the XY table and the rotating motor. A development drawing representing the stent of the structure shown in FIG. 5 was input in the computer with design software installed therein.

The XY table and rotating motor were driven in accordance with design data delivered from the computer. By operating the laser to emit a laser beam, the pipe was machined into a stent structure of the configuration shown in FIG. 1.

It is noted that a mandrel was inserted into the pipe to prevent the laser beam from penetrating throughout the pipe. Laser machining conditions for the metal pipe included a current of 25 A, an output of 1.5 W, and a drive speed of 10 mm/min. The machine is not limited to the above-mentioned system and there may be used a laser marker of the galvanometer system adapted to be driven by a laser machining device.

Only one annular unit at one end of the stent structure was dipped in a stainless steel chemical polishing solution at about 98° C. for about 5 minutes. The chemical polishing solution used herein was a solution containing a mixture of hydrochloric acid and nitric acid as a main component, an organic sulfur compound and a surfactant, which was commercially available as Sunbit 505 from Sanshin Chemical Industry K.K. Similarly, one annular unit at the opposite end of the stent structure was dipped in the chemical polishing solution for about 5 minutes. By this dipping treatment, the wall thickness of members of the end annular units was reduced as compared with the remaining annular units.

In this way, there was prepared a stent according to the invention having the configuration shown in FIGS. 1 to 3. In the stent, ellipsoidal elements had a major axis length of 2.6 mm and a minor axis length of 0.72 mm. Four ellipsoidal elements were circumferentially tied into an annular unit. Six elements (or annular units) were arranged on a straight line with an axial spacing of 0.2 mm. The stent had an overall axial length of 16.6 mm. The tie members connecting the elements had a length of 0.38 mm. The connecting members connecting the annular units had a length of 2.8 mm and a width of 0.2 mm. The elements had a width of 0.17 mm near axially opposed ends (bend points) and a width of 0.2 mm in the remaining zones. The elements had a cross-sectional area of 0.014 mm$^2$ near axially opposed ends (bend points) and a cross-sectional area of 0.02 mm$^2$ in the remaining zones. Members of the annular units in an intermediate region had a wall thickness of 0.1 mm while members of the end annular units had a wall thickness of 0.08 mm. The stent (or annular units) had an outer diameter of 1.4 mm.

The stent was mounted on a balloon of a balloon catheter. A radiographic contrast medium was forced into the balloon catheter under a pressure of 10 kg/cm$^2$ to inflate the balloon, thereby expanding the stent substantially uniformly. The expanded stent had an outer diameter of 3.2 mm. In the expanded condition, the major axis distance of ellipsoidal elements was shortened from 2.6 mm to about 1.6 mm while the minor axis distance was elongated from 0.72 mm to 2.1 mm. As the major and minor axis distances were inverted, the elements were deformed from the ellipsoidal shape to the generally rhombic shape as shown in FIGS. 6 and 8. Nevertheless, the overall length of the stent was little shortened because the respective annular units were connected by the relatively long connecting members parallel to the stent axis. An actual shortening was the distance by which the annular units at opposite ends of the stent were shortened. Since the major axis distance of ellipsoidal shape was shortened from 2.6 mm to 1.6 mm, a shortening corresponding to one-half of the difference 1 mm, that is, 0.5 mm occurred at one end of the stent. A total shortening of 1 mm occurred at both ends of the stent. This corresponds to only 6% of the stent overall length of 16.5 mm, which will give rise to no substantial problem in actual clinical application.

Example 2

A stent structure was prepared by the same procedure as in Example 1 until the end of laser machining.

Two annular units at one end of the stent structure were dipped in the stainless steel chemical polishing solution at about 98° C. for about 5 minutes, and two annular units at the other end of the stent structure were similarly dipped in the chemical polishing solution for about 5 minutes. Furthermore, only one annular unit at one end of the stent structure was dipped in the chemical polishing solution for about 3 minutes, and only one annular unit at the other end of the stent structure was similarly dipped in the chemical polishing solution for about 3 minutes.

In the resulting stent, members of two annular units at a central region of the stent had the maximum wall thickness, members of two end annular units had the minimum wall thickness, and members of annular units next to the end ones had an intermediate wall thickness.

Example 3

A metal pipe of stainless steel SUS 316L having a diameter of 1.4 mm and a gage of 0.10 mm was cut to a length of 50 mm.

A stent was prepared by hollowing out a metal pipe to leave a stent skeleton by laser machining.

A laser machining device used was a YAG laser model SL116E manufactured by NEC. The metal pipe was mounted on a jig equipped with a rotating motor by means of a chuck mechanism such that the pipe might be kept aligned. The jig was set on a numerically controlled XY table. The XY table and the rotating motor were connected to a personal computer such that an output of the computer was delivered to a numerical controller of the XY table and the rotating motor. A development drawing representing the stent of the structure shown in FIG. 9 was input in the computer with design software installed therein.

The XY table and rotating motor were driven in accordance with design data delivered from the computer. By operating the laser to emit a laser beam, the pipe was machined into a stent structure of the configuration shown in FIG. 8.

It is noted that a mandrel was inserted into the pipe to prevent the laser beam from penetrating throughout the pipe. Laser machining conditions for the metal pipe included a current of 25 A, an output of 1.5 W, and a drive speed of 10 mm/min.

One end region 20a of the stent structure (including one and a half of annular unit) was dipped in a stainless steel chemical polishing solution at about 98° C. for about 5 minutes. The chemical polishing solution used herein was a solution containing a mixture of hydrochloric acid and nitric acid as a main component, an organic sulfur compound and a surfactant, which was commercially available as Sunbit 505 from Sanshin Chemical Industry K.K. Similarly, another end region 20c of the stent structure (including one and a half of annular unit) was dipped in the chemical polishing solution for about 5 minutes. By this dipping treatment, the wall thickness of members of the end annular units was reduced as compared with the remaining annular units.

In this way, there was prepared a stent according to the invention having the configuration shown in FIG. 9. In the stent, the elements were generally rhombus shaped except for end elements the outer half of which was ellipsoidal. The elements had a major axis (longer diagonal line) length of 2.6 mm and a minor axis (shorter diagonal line) length of 0.6 mm. Five rhombic elements were circumferentially tied into an annular unit by five tie members (three short ones and two long ones). The stent had an overall axial length of 16 mm. Among the tie members tying the elements, the short ones had a length of 0.25 mm and the long ones had a length of 0.4 mm. The elements had a width of 0.17 mm near axially opposed ends (bend points) and a width of 0.2 mm in the remaining zones. The elements had a cross-sectional area of 0.015 $mm^2$ near axially opposed ends (bend points) and a cross-sectional area of 0.02 $mm^2$ in the remaining zones.

Eight annular units were serially arranged along the stent axis while one element of one annular unit penetrated between adjacent elements of an adjacent annular unit (near the tie member) to provide an axial overlap of 0.7 mm. The center-to-center distance between elements of adjacent annular units was 1.9 mm. The connecting members connecting the annular units had a length of 2.0 mm and a width of 0.2 mm and were inclined at an angle of 12° relative to the stent axis.

Members of the annular units in the intermediate region 20b had a wall thickness of 0.1 mm while members of the end annular units in the end regions 20a and 20c had a wall thickness of 0.08 mm. The stent (or annular units) had an outer diameter of 1.4 mm.

The stent was mounted on a balloon of a balloon catheter. A radiographic contrast medium was forced into the balloon catheter under a pressure of 10 kg/$cm^2$ to inflate the balloon, thereby expanding the stent substantially uniformly. The expanded stent had an outer diameter of 3.0 mm. In the expanded condition, the major axis distance of rhombic elements was shortened from 2.6 mm to about 1.5 mm while the minor axis distance was elongated from 0.6 mm to 1.7 mm. As the major and minor axis distances were inverted, the elements were deformed into a more bulged rhombic shape. Nevertheless, the overall length of the stent was little shortened because the respective annular units were connected by the relatively long connecting members parallel to each other. An actual shortening was the distance by which the annular units at opposite ends of the stent were shortened. Since the major axis distance of rhombic shape was shortened from 2.6 mm to 1.5 mm, a shortening corresponding to one half of the difference 1.1 mm, that is, 0.55 mm occurred at one end of the stent. A total shortening of 1.1 mm occurred at both ends of the stent. This corresponds to only 6% of the stent overall length of 16 mm, which will give rise to no substantial problem in actual clinical application.

Example 4

A metal pipe of stainless steel SUS 316L having a diameter of 1.4 mm and a gage of 0.08 mm was cut to a length of 50 mm.

A stent was prepared by hollowing out a metal pipe to leave a stent skeleton by laser machining.

A laser machining device used was a YAG laser model SL116E manufactured by NEC. The metal pipe was mounted on a jig equipped with a rotating motor by means of a chuck mechanism such that the pipe might be kept aligned. The jig was set on a numerically controlled XY table. The XY table and the rotating motor were connected to a personal computer such that an output of the computer was delivered to a numerical controller of the XY table and the rotating motor. A development drawing representing the stent of the structure shown in FIG. 12 was input in the computer with design software installed therein.

The XY table and rotating motor were driven in accordance with design data delivered from the computer. By operating the laser to emit a laser beam, the pipe was machined into a stent structure.

It is noted that a mandrel was inserted into the pipe to prevent the laser beam from penetrating throughout the pipe. Laser machining conditions for the metal pipe included a current of 25 A, an output of 1.5 W, and a drive speed of 10 mm/min.

In this way, there was prepared a stent according to the invention having the configuration shown in FIG. 12. In the stent, the elements were generally rhombus shaped except for end elements the outer half of which was ellipsoidal. The elements had a major axis (longer diagonal line) length of 3.8 mm and a minor axis (shorter diagonal line) length of 0.65 mm. Four rhombic elements were circumferentially tied into an annular unit by four tie members (two short ones and two long ones). The stent had an overall axial length of 19.3 mm. Among the tie members tying the elements, the short ones had a length of 0.3 mm and the long ones had a length of 0.6 mm. The elements had a width of 0.15 mm near axially opposed ends (bend points) and a width of 0.25 mm in the remaining zones. The elements had a cross-sectional area of 0.12 $mm^2$.

Six annular units were serially arranged along the stent axis while one element of one annular unit penetrated between adjacent elements of an adjacent annular unit (near the tie member) to provide an axial overlap of 0.7 mm. One annular unit has four elements. The center-to-center distance between elements of adjacent annular units was 3.1 mm. The connecting members connecting the annular units had a length of 3.2 mm and a width of 0.15 mm and were inclined at an angle of 12° relative to the stent axis.

The stent was mounted on a balloon of a balloon catheter. A radiographic contrast medium was forced into the balloon catheter under a pressure of 10 kg/$cm^2$ to inflate the balloon, thereby expanding the stent substantially uniformly. The expanded stent had an outer diameter of 3.0 mm. In the expanded condition, the major axis distance of rhombic elements was shortened from 3.8 mm to about 2.5 mm while the minor axis distance was elongated from 0.65 mm to 2.9 mm. As the major and minor axis distances were inverted, the elements were deformed into a more bulged rhombic shape. Nevertheless, the overall length of the stent was little shortened because the respective annular units were connected by the relatively long connecting members parallel to each other. An actual shortening was the distance by which the annular units at opposite ends of the stent were shortened. Since the major axis distance of rhombic shape was shortened from 3.8 mm to 2.5 mm, a shortening corresponding to one-half of the difference 1.3 mm, that is, 0.65 mm occurred at one end of the stent. A total shortening of 1.3 mm occurred at both ends of the stent. This corresponds to only 6% of the stent overall length of 19.3 mm, which will give rise to no substantial problem in actual clinical application.

There has been described a stent in the form of a generally tubular member having a diameter allowing for insertion into a body passageway and radially expandable upon application of a radially outward extending force from the interior of the tubular member wherein a plurality of generally ellipsoidal or polygonal elements which are elongate in an axial direction of the stent and have a center opening are arranged so as to surround the stent axis, circumferentially opposed ends of adjacent elements are connected by tie members to construct an annular unit, a plurality of such annular units are arranged in an axial direction of the stent, and a tie member of one annular unit is connected to a tie member of an adjacent annular unit by at least one connecting member.

Since the generally ellipsoidal or polygonal, centrally open elements each constructing an independent closed cell are circumferentially connected to form an annular unit, the annular unit exerts a strong expansion retaining force. Since the axial center of a side of one element is connected to the axial center of a side of an adjacent element by each of the relatively short tie members, which remain substantially unchanged upon expansion of the stent, the expanding force acts on each element at its center so that the elements may be uniformly expanded. Since a tie member of one annular unit is connected to a tie member of an adjacent annular unit by each of the axially extending connecting member, which remain substantially unchanged upon expansion of the stent, the overall length of the stent changes little upon expansion.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A stent for body implanting in the form of a generally tubular member having an axis and a diameter allowing for insertion into a body passageway and radially expandable upon application of a radially outward extending force from the interior of the tubular member, said stent comprising a series of annular units arranged in an axial direction of the stent, each said annular unit comprising a plurality of closed cell generally rhombic elements arranged so as to surround the stent axis, said elements being elongate in an axial direction of the stent and having a center generally rhombic opening, and a corresponding plurality of tie members each connecting circumferentially opposed ends of adjacent elements, adjacent annular units being interconnected at their tie members by at least one connecting member, and wherein two adjacent generally rhombic elements of one annular unit and the tie member connecting them define therebetween a generally V-shaped or trapezoidal space into which an axial end portion of one generally rhombic element of an adjacent annular unit extends.

2. A stent of claim 1 wherein annular units in end regions of the stent have a lesser wall thickness than annular units in an intermediate region.

3. The stent of claim 1 wherein said generally rhombic elements have a smaller cross-sectional area at axially opposed ends than the remainder of each said rhombic element.

4. The stent of claim 1 wherein adjacent annular units are interconnected by only one connecting member.

5. The stent of claim 4 wherein said connecting members are helically spaced apart with respect to the axis of the stent.

6. The stent of claim 1 wherein the annular units are made of a metal material and have been annealed.

7. The stent of claim 1 wherein when the stent is longitudinally cut parallel to the stent axis, the connecting members are inclined at an angle with respect to a longitudinal direction of the stent.

8. The stent of claim 1 wherein said elements of the annular units at axially opposed ends of the stent have a generally semi-ellipsoidal shape at their outer half.

9. The stent of claim 1 wherein an axial center of a side of one generally rhombic element is connected to an axial center of a side of an adjacent generally rhombic element by one of the tie members.

10. A stent for body implanting in the form of a generally tubular member having an axis and a diameter allowing for insertion into a body passageway and radially expandable upon application of a radially outward extending force from the interior of the tubular member, said stent comprising a series of annular units arranged in an axial direction of the stent, each said annular unit comprising a plurality of generally ellipsoidal or polygonal elements arranged so as to surround the stent axis, said elements being elongate in an axial direction of the stent and having a center opening, and a corresponding plurality of tie members each connecting circumferentially opposed ends of adjacent elements, adjacent annular units being interconnected at their tie members by at least one connecting member, and wherein two adjacent generally ellipsoidal or polygonal elements of one annular unit and the tie member connecting them define therebetween a space into which an axial end of one generally ellipsoidal or polygonal element of an adjacent annular unit extends and wherein units adjacent annular units are interconnected by only one connecting member.

11. The stent of claim 10 wherein annular units in end regions of the stent have a lesser wall thickness than annular units in an intermediate region.

12. The stent of claim 10 wherein said generally ellipsoidal or polygonal elements have a smaller cross-sectional area at axially opposed ends than the remainder of each said element.

13. The stent of claim 10 wherein said connecting members are helically spaced apart with respect to the axis of the stent.

14. The stent of claim 10 wherein the annular units are made of a metal material and have been annealed.

15. The stent of claim 10 wherein when the stent is longitudinally cut parallel to the stent axis, the connecting members are inclined at an angle with respect to a longitudinal direction of the stent.

16. The stent of claim 10 wherein said elements of the annular units at axially opposed ends of the stent have a generally semi-ellipsoidal shape at their outer half.

17. The stent of claim 10 wherein an axial center of a side of one generally ellipsoidal or polygonal element is connected to an axial center of a side of an adjacent generally ellipsoidal or polygonal element by one of the tie members.

18. A stent for body implanting in the form of a generally tubular member having an axis and a diameter allowing for insertion into a body passageway and radially expandable upon application of a radially outward extending force from the interior of the tubular member, said stent comprising a series of annular units arranged in an axial direction of the stent, each said annular unit comprising a plurality of generally ellipsoidal or polygonal elements arranged so as to surround the stent axis, said elements being elongate in an axial direction of the stent and having a center opening, and a corresponding plurality of tie members each connecting circumferentially opposed ends of adjacent elements, adjacent annular units being interconnected at their tie members by at least one connecting member, and wherein two adjacent generally ellipsoidal or polygonal elements of one annular unit and the tie member connecting them define therebetween a space into which an axial end of one generally ellipsoidal or polygonal element of an adjacent annular unit extends and wherein when the stent is longitudinally cut parallel to the stent axis, the connecting members are inclined at an angle with respect to a longitudinal direction of the stent.

19. The stent of claim 18 wherein annular units in end regions of the stent have a lesser wall thickness than annular units in an intermediate region.

20. The stent of claim 18 wherein said generally ellipsoidal or polygonal elements have a smaller cross-sectional area at axially opposed ends than the remainder of each said element.

21. The stent of claim 18 wherein adjacent annular units are interconnected by only one connecting member.

22. The stent of claim 18 wherein said connecting members are helically spaced apart with respect to the axis of the stent.

23. The stent of claim 18 wherein the annular units are made of a metal material and have been annealed.

24. The stent of claim 18 wherein said elements of the annular units at axially opposed ends of the stent have a generally semi-ellipsoidal shape at their outer half.

25. The stent of claim 18 wherein an axial center of a side of one generally ellipsoidal or polygonal element is connected to an axial center of a side of an adjacent generally ellipsoidal or polygonal element by one of the tie members.

26. The stent of claim 16 wherein the two adjacent rhombic element of said one annular unit are laterally offset from the one rhombic element of the adjacent annular unit such that the rhombic elements are partially overlapped in the axial direction of the stent.

* * * * *

UNITED STATES PATENT AND TRADEMARK OFFICE
CERTIFICATE OF CORRECTION

PATENT NO. : 6,200,337 B1
DATED : March 13, 2001
INVENTOR(S) : Yousuke Moriuchi et al.

It is certified that error appears in the above-identified patent and that said Letters Patent is hereby corrected as shown below:

Claim 26,
Line 1, "16" is deleted, and -- 1 -- is inserted in its place.

Signed and Sealed this

Eighteenth Day of December, 2001

Attest:

Attesting Officer

JAMES E. ROGAN
Director of the United States Patent and Trademark Office